United States Patent [19]

Edwards et al.

[11] Patent Number: 4,948,734

[45] Date of Patent: Aug. 14, 1990

[54] NOVEL ISOLATES OF BACILLUS THURINGIENSIS HAVING ACTIVITY AGAINST NEMATODES

[75] Inventors: David L. Edwards, Del Mar; Jewel Payne; George G. Soares, both of San Diego, all of Calif.

[73] Assignee: Mycogen Corporation, San Diego, Calif.

[21] Appl. No.: 84,653

[22] Filed: Aug. 12, 1987

[51] Int. Cl.$^5$ .................. C12R 1/07; C12P 21/00; A01N 63/00
[52] U.S. Cl. ..................... 435/252.5; 435/252.31; 435/832; 435/172.3; 435/240.4; 424/93; 514/2; 530/370; 800/200; 935/63; 935/64
[58] Field of Search ............... 435/252.31, 832, 252.5; 424/93; 530/370; 514/2

[56] References Cited

U.S. PATENT DOCUMENTS 4,781,922  11/1988  Bone ..................................... 424/92

OTHER PUBLICATIONS

Bone et al., 1985, Exp. Parasitology 60:314–322.
Whiteley et al., 1986, Ann. Rev. Microbiol. 40:549–576.
Aronson et al., 1986, Microbiological Reviews 50:1–24.
Carlton et al., 1985, In Molecular Biology of Bacilli. vol. II, p. 212.
Vaeck et al., Jul. 1987, Nature 328:33–37.
Bulla et al., 1985, In Molecular Biology of the Bacilli. vol. II, pp. 192–197.
Prichard, R. K., C. A. Hall, J. D. Kelly, I. C. A. Martin and A. D. Donald, 1980, the Problem of Anthelmintic Resistance in Nematodes, Austr. Vet. J. 56:239–251.
Coles, G. C., 1986, anthelmentic Resistance in Sheep, In Veterinary Clinics of North America: Food Animal Practice, vol. 2:423–432. Herd, R. P. (ed.), W. P. Saunders, New York.
Bottjer, Kurt P., Leon W. Bone, and Sarjeet S. Gill. 1985, Nematoda:Susceptibility of the Egg to *Bacillus thuringiensis* Toxins, Experimental Parasitology 60:239–244.
Ignoffo, C. M. and V. H. Dropkin, Deleterious Effects of the thermostable Toxin of *Bacillus thuringiensis* on Species of Soil–Inhabiting, Myceliophagus, and Plant Parasitic Nematodes, J. Kans. Entomol. Soc. 50:394–398, 1977.
Ciordia, H. and W. E. Bizzell, Jour. of Parasitology 47:41 [abstract] 1961.

*Primary Examiner*—Charles F. Warren
*Assistant Examiner*—P. Rhodes
*Attorney, Agent, or Firm*—Saliwanchik & Saliwanchik

[57] ABSTRACT

The invention concerns novel isolates of *Bacillus thuringiensis* (*B.t.*) which contain a toxin(s) which is active against adult nematode worms and larvae. this B.t. toxin(s) can be used to treat animals and plants hosting susceptible nematodes.

20 Claims, No Drawings

NOVEL ISOLATES OF BACILLUS THURINGIENSIS HAVING ACTIVITY AGAINST NEMATODES

BACKGROUND OF THE INVENTION

Regular use of chemicals to control unwanted organisms can select for drug resistant strains. This has occurred in many species of economically important insects and has also occurred in nematodes of sheep, goats, and horses. The development of drug resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. 1980. The problem of anthelmintic resistance in nematodes. Austr. Vet. J. 56:239–251; Coles, G. C. 1986. Anthelmintic resistance in sheep. In Veterinary Clinics of North America: Food Animal Practice. Vol 2:423–432. Herd, R. P. (ed). W. B. Saunders, New York). There are more than 100,000 described species of nematodes.

The bacterium *Bacillus thuringiensis* (B.t.) produces a polypeptide toxin that has been shown to have activity against a rapidly growing number of insect species. The earlier observations of toxicity only against lepidopteran insects have been expanded with descriptions of B.t. isolates with toxicity to dipteran and coleopteran insects. These toxins are deposited as crystalline inclusions within the organism. Many strains of B.t. produce crystalline inclusions with no demonstrated toxicity to any insect tested.

A small number of research articles have been published about the effects of delta endotoxins from *B. thuringiensis* species on the viability of nematode eggs. Bottjer, Bone and Gill (Experimental Parasitology 60:239–244, 1985) have reported that *B.t. kurstaki* and *B.t. israelensis* were toxic in vitro to eggs of the nematode *Trichostrongylus colubriformis*. In addition, 28 other B.t. strains were tested with widely variable toxicities. The most potent had $LD_{50}$ values in the nanogram range. Ignoffo and Dropkin (Ignoffo, C.M. and Dropkin, V.H. J. Kans. Entomol. Soc. 50:394–398, 1977) have reported that the thermostable toxin from *Bacillus thuringiensis* (beta exotoxin) was active against a free-living nematode, *Panagrellus redivivus* (Goodey): a plant-parasitic nematode, *Meloidogyne incognita* (Chitwood): and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

At the present time there is a need to have more effective means to control the many nematodes that cause considerable damage to susceptible hosts.

BRIEF SUMMARY OF THE INVENTION

The subject invention concerns five novel isolates of *Bacillus thuringiensis* that are active against nematodes tested, for example, *Caenorhabditis elegans* and *Haemonchus contortus*. Advantageously, and surprisingly, these novel B.t. isolates are active against the larvae and adult forms of the nematodes.

The B.t. isolates of the invention can be grown and the delta endotoxin that is produced recovered by standard procedures. The recovered toxin can be formulated using standard procedures associated with the use of nematocidal products.

The novel B.t. isolates are named B.t. strain PS-17, B.t. strain PS-33F2, B.t. strain PS-52A1, B.t. strain PS-63B, and B.t. strain PS-69D1.

DETAILED DISCLOSURE OF THE INVENTION

The novel B.t. isolates of the subject invention have been deposited in the Agricultural Research Service Patent Culture Collection (NRRL), Northern Regional Research Center, 1815 North University Street, Peoria, Ill. 61604, USA.

| Culture | Repository No. | Deposit Date |
| --- | --- | --- |
| B.t. strain PS-17 | NRRL B-18243 | July 28, 1987 |
| B.t. strain PS-33F2 | NRRL B-18244 | July 28, 1987 |
| B.t. strain PS-52A1 | NRRL B-18245 | July 28, 1987 |
| B.t. strain PS-63B | NRRL B-18246 | July 28, 1987 |
| B.t. strain PS-69D1 | NRRL B-18247 | July 28, 1987 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing a culture. The depositor acknowledges the duty to replace a deposit should the depository be unable to furnish a sample when requested, due to the condition of the deposit. All restrictions on the availability to the public of the subject culture deposits will be irrevocably removed upon the granting of a patent disclosing them.

The novel B.t. isolates of the invention show activity against tested nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis, and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

The toxins from the novel B.t. isolates of the invention are useful as nematocides for the control of soil nematodes and plant parasites selected from the genera Bursaphalenchus, Criconemella, Ditylenchus, Globodera, Helicotylenchus, Heterodera, Melodiogyne, Pratylenchus, Radolpholus, Rotelynchus, or Tylenchus.

Alternatively, because some plant parasitic nematodes are obligate parasites, genes coding for nematocidal B.t. toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387-399, 1984).

The B.t. toxins of the invention can be administered orally in a unit dosage form such as a capsule, bolus or tablet, or as a liquid drench when used as an anthelmintic in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraruminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

In addition to having anthelminthic activity within the digestive tract of mammals, spores from nematocidal B.t. isolates will pass through the animals' digestive tract, germinate and multiply in the feces, and thereby provide additional control of nematode larvae which hatch and multiply therein.

The gene(s) from the novel B.t. isolates of the subject invention can be introduced into microbes capable of occupying, surviving in and proliferating in the phytosphere of plants according to the procedures disclosed in European Patent Application 0 200 344. Upon ingestion of such a plant by an animal hosting a nematode, the nematode-active toxin becomes available in the animal host to control the nematode infestation.

Following are examples which illustrate procedures, including the best mode, for practicing the invention. These examples should not be construed as limiting. All percentages are by weight and all solvent mixture proportions are by volume unless otherwise noted.

EXAMPLE 1 - CULTURING B.t. ISOLATES

A subculture of a B.t. isolate can be used to inoculate the following medium, a peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4$—$7H_2O$ | 2.46 g |
| $MnSO_4$—$H_2$ | 0.04 g |
| $ZnSO_4$—$7H_2O$ | 0.28 g |
| $FeSO_4$—$7H_2O$ | 0.40 g |
| $CaCl_2$ Solution (100 ml) | |
| $CaCl_2$—$2H_2O$ | 3.66 g |
| pH 7.2 | |

The salts solution and $CaCl_2$ solution are filtersterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The Bt spores and crystals, obtained in the above fermentation, can be isolated by procedures well known in the art. A frequently-used procedure is to subject the harvested fermentation broth to separation techniques, e.g., centrifugation.

EXAMPLE 2 - ACTIVITY OF BCILLUS THURINGIENSIS ISOLATES AGAINST CAENORHABDITIS ELEGANS

A fresh isolate of *C. elegans* was cultured as described by Simpkin and Coles (J. Chem. Tech. Biotechnol. 31:66-69, 1981) with 5 mg ampicillin/100 ml in STERILIN multiwell plates. Each well contained approximately 150 worms. The B.t. isolates were grown until sporulation was completed. Samples in fermentation broth were then irradiated with 10 Kilograys of gamma radiation from a $^{60}$Co source. Under these conditions no viable cells remained. One ml aliquots of B.t. samples were centrifuged at 11,000×g/10 min and the supernatant removed. Pellets were washed twice in nematode washing buffer (Brenner, S. Genetics 77:71-94, 1974) and resuspended in one ml buffer. Aliquots of supernatant or resuspended pellet material were added to suspensions of worms and incubated at 20° C. for 7 days, after which the wells were observed and the number of live worms relative to controls containing aliquots of *Bacillus subtilis* cultures was noted. All experiments were done in duplicate. The results are as follows:

| Strain | | Activity |
|---|---|---|
| Control (*B. subtilis*) | | All worms active |
| B.t. PS-17 | 0.1 ml supernatant | Many active worms |
| | 0.5 ml supernatant | Some active worms |
| | 0.1 ml pellet | Few active worms |
| | 0.5 ml pellet | No live worms |
| B.t. PS-33F2 | 0.1 ml supernatant | Many active worms |
| | 0.5 ml supernatant | Many active worms |
| | 0.1 ml pellet | <1% live worms |
| | 0.5 ml pellet | No live worms |
| B.t. PS-52A1 | 0.1 ml supernatant | Many active worms |
| | 0.5 ml supernatant | Many active worms |
| | 0.1 ml pellet | No live worms |
| | 0.5 ml pellet | No live worms |
| B.t. PS-63B | 0.1 ml supernatant | Many active worms |
| | 0.5 ml supernatant | Many active worms |
| | 0.1 ml pellet | Many active worms |
| | 0.5 ml pellet | Few active worms |
| B.t. PS-69D1 | supernatant | Not assayed |
| | 1.0 ml pellet | No live worms |

EXAMPLE 3 - ACTIVITY OF DELTA ENDOTOXIN PREPARATIONS OF BACILLUS THURINGIENSIS ISOLATES ON C. ELEGANS

Isolates of *Bacillus thuringiensis* were grown until sporulation was completed. Delta endotoxin crystals were prepared from these cultures on sodium bromide gradients as described by Pfannenstiel et al. (Pfannenstiel, M. A., Ross, E. J., Kramer, V. C. and Nickerson, K. W. 1984, FEMS Microbiol. Lett. 21:39-42). The toxin crystal preparations were then irradiated with 10 Kilograys of gamma radiation from a $^{60}$Co source to inactivate any bacterial spores that may have been in the preparation. The protein content of the crystal preparations was determined by the method of Lowry (Lowry, O. H., Roseborough, N. J., Farr, A. L. and Randall, R. J., J. Biol. Chem. 193:265-275, 1951) and 100 μg of material was added to the test wells. All experiments were done in duplicate. The results are as follows:

| Strain | Activity |
|---|---|
| B.t. PS-17 | No live worms |
| B.t. PS-33F2 | <1% live worms |
| B.t. PS-52A1 | <1% live worms |
| B.t. PS-63B | No live worms |
| B.t. PS-69D1 | <1% live worms |

EXAMPLE 4 - ACTIVITY OF BACILLUS THURINGIENSIS ISOLATES AGAINST THE SHEEP NEMATODE HAEMONCHUS CONTORTUS

A one ml aliquot of B.t. cell suspension was washed twice with water and resuspended in 10 ml of water. One ml of this suspension was added to 1 ml heat-treated lyophilized *E. coli* (0.75 mg/ml) in a STERILIN multiwell plate and eggs of a levamisol/benzimidazole resistant strain of *H. contortus* were counted in each well. Each sample was replicated 4 times. Per cent dead larvae were calculated relative to control wells that contained *B. subtilis*. The results are as follows:

| Strain | Activity (% dead larvae) |
|---|---|
| B.t. PS-17 | 59 |
| B.t. PS-33F2 | 12 |
| B.t. PS-52A1 | 90 |
| B.t. PS-63B | 83 |

We claim:

1. A *Bacillus thuringiensis* isolate active against nematodes, said isolate selected from *B. thuringiensis* strain PS-17, *B. thuringiensis* strain PS-33F2, *B. thuringiensis* strain PS-52A1, *B. thuringiensis* strain PS-63B, and *B. thuringiensis* strain PS-69D1.

2. *B. thuringiensis* strain PS-17, according to claim 1.

3. *B. thuringiensis* strain PS-33F2, according to claim 1.

4. *B. thuringiensis* strain PS-52A1, according to claim 1.

5. *B. thuringiensis* strain PS-63B, according to claim 1.

6. *B. thuringiensis* strain PS-69D1, according to claim 1.

7. A process for controlling nematodes which comprises contacting said nematodes with a nematode-controlling effective amount of a toxin produced by a *B. thuringiensis* isolate selected from *B. thuringiensis* strain PS-17, *B. thuringiensis* strain PS-33F2, *B. thuringiensis* strain PS-52A1, *B. thuringiensis* strain PS-63B, and *B. thuringiensis* strain PS-69D1.

8. A process, according to claim 7, wherein the toxin is produced by *B. thuringiensis* PS-17.

9. A process, according to claim 7, wherein the toxin is produced by *B. thuringiensis* PS-33F2.

10. A process, according to claim 7, wherein the toxin is produced by *B. thuringiensis* PS-52A1.

11. A process, according to claim 7, wherein the toxin is produced by *B. thuringiensis* PS-63B.

12. A process, according to claim 7, wherein the toxin is produced by *B. thuringiensis* PS-69D1.

13. A process, according to claim 7, wherein the nematode is *Caenorhabditis elegans* or *Haemonchus contortus*.

14. A process for treating an animal hosting a nematode which comprises administering to said animal host a nematode-controlling effective amount of a toxin produced by a *B. thuringiensis* isolate selected from *B. thuringiensis* strain PS-17, *B. thuringiensis* strain PS-33F2,

*B. thuringiensis* strain PS-52A1, *B. thuringiensis* strain PS-63B, and *B. thuringiensis* strain PS-69D1.

15. A process, according to claim 14, wherein the toxin is produced by *B. thuringiensis* PS-17.

16. A process, according to claim 14, wherein the toxin is produced by *B. thuringiensis* PS-33F2.

17. A process, according to claim 14, wherein the toxin is produced by *B. thuringiensis* PS-52A1.

18. A process, according to claim 14, wherein the toxin is produced by *B. thuringiensis* PS-63B.

19. A process, according to claim 14, wherein the toxin is produced by *B. thuringiensis* PS-69D1.

20. A process, according to claim 14, wherein the nematode is selected from the genera Haemonchus or Caenorhabditis.

* * * * *

UNITED STATES PATENT AND TRADEMARK OFFICE
CERTIFICATE OF CORRECTION

PATENT NO. : 4,948,734

DATED : August 14, 1990

INVENTOR(S) : David L. Edwards, Jewel Payne, George G. Soares

It is certified that error appears in the above-identified patent and that said Letters Patent is hereby corrected as shown below:

Abstract: line 3: ". this" should read --. This--.
Title: "BACILLUS THURINGIENSIS" should read --*BACILLUS THURINGIENSIS*--.
Column 3: line 31: "weight, The capsules" should read --weight. The capsules--; line 64 & 65 "for administration such" should read --for administration, such--.
Column 6: line 1: "*BCILLUS*" should read --*BACILLUS*--.

Signed and Sealed this

Twenty-first Day of July, 1992

*Attest:*

DOUGLAS B. COMER

*Attesting Officer*   *Acting Commissioner of Patents and Trademarks*